(12) United States Patent
Schneider (10) Patent No.: US 8,968,593 B2
(45) Date of Patent: Mar. 3, 2015

(54) PRODUCT AND METHOD FOR ENHANCING THE BIOPHYSICAL EFFECTS OF WATER

(71) Applicant: David Schneider, Chemult, OR (US)

(72) Inventor: David Schneider, Chemult, OR (US)

( * ) Notice: Subject to any disclaimer, the term of this patent is extended or adjusted under 35 U.S.C. 154(b) by 0 days.

(21) Appl. No.: 14/304,907

(22) Filed: Jun. 14, 2014

(65) Prior Publication Data

US 2014/0361215 A1    Dec. 11, 2014

Related U.S. Application Data

(62) Division of application No. 13/436,731, filed on Mar. 30, 2012, now Pat. No. 8,753,531.

(60) Provisional application No. 61/470,120, filed on Mar. 31, 2011.

(51) Int. Cl.
| | | |
|---|---|---|
| *C02F 5/02* | (2006.01) | |
| *C02F 5/08* | (2006.01) | |
| *A61K 35/08* | (2006.01) | |
| *C02F 1/68* | (2006.01) | |

(52) U.S. Cl.
CPC .. *A61K 35/08* (2013.01); *C02F 1/68* (2013.01)
USPC ......................................... 252/175; 252/181

(58) Field of Classification Search
USPC ................................................ 252/175, 181
See application file for complete search history.

(56) References Cited

U.S. PATENT DOCUMENTS

| | | | | |
|---|---|---|---|---|
| 2,614,055 | A | * | 10/1952 | De Senarclens ................... 241/4 |
| 4,279,756 | A | * | 7/1981 | Weiss et al. .................... 210/667 |
| 4,708,814 | A | * | 11/1987 | Stewart ......................... 252/181 |
| 4,776,963 | A | * | 10/1988 | Inagaki et al. ................ 210/764 |
| 4,983,286 | A | * | 1/1991 | Inagaki et al. ............. 210/257.1 |
| 6,656,439 | B2 | * | 12/2003 | Poncelet et al. ............ 423/239.1 |
| 2002/0074290 | A1 | * | 6/2002 | Jensen .......................... 210/668 |

FOREIGN PATENT DOCUMENTS

JP           01143608 A   *   6/1989   ............. B01D 21/01

* cited by examiner

*Primary Examiner* — Nicole M Buie-Hatcher
*Assistant Examiner* — M. Reza Asdjodi
(74) *Attorney, Agent, or Firm* — William C. Milks, III

(57) ABSTRACT

A product-by-process produces a product having a vibrational frequency to balance the chemistry of water when untreated water is exposed to the product to thereby enhance the biophysical properties of water, without adding any compound to the water. The result of the exposure is that the physical properties of specific gravity, conductivity, and resistivity of water are modified, and the biophysical properties of the treated water in organisms such as humans, including but not limited to hydration, oxygenation, and detoxification, are enhanced as verified by human clinical tests.

15 Claims, 3 Drawing Sheets

PRODUCT AND METHOD FOR ENHANCING THE BIOPHYSICAL EFFECTS OF WATER

CROSS-REFERENCE TO RELATED PATENT APPLICATION

This application relates to U.S. Provisional Patent Application No. 61/470,120 filed on Mar. 31, 2011, entitled PRODUCT AND METHOD FOR ENHANCING THE BIOPHYSICAL EFFECTS OF WATER, which is hereby incorporated herein in its entirety by this reference.

BACKGROUND OF THE INVENTION

1. Field of the Invention

The present invention relates generally to water ($H_2O$) and, more particularly, to improving the biophysical properties of water for use by organisms. Specifically, various examples of the present invention provide a product-by-process that produces a vibrational frequency to balance the chemistry of water when untreated water is exposed to the product to thereby enhance the biophysical properties of water, without adding any compound to the water. The result of the exposure is that the physical properties of water including specific gravity, conductivity, and resistivity are modified, and the biophysical properties of the treated water in organisms such as humans, including but not limited to hydration, oxygenation, and detoxification, are enhanced as verified by human clinical tests. In one example, a product is provided to treat water wherein the specific gravity of the water was reduced below 1.009 and cellular toxins were reduced on average by at least 18.8% but not less than 4.0-6.0% in normal persons having relatively low levels of toxins.

2. Description of the Prior Art

Water is necessary for life as we know it. Without water, life would not exist on Earth. Water is an essential nutrient that is involved in essentially every function of living organisms.

Water constitutes a high percentage of living organisms. For example, adult human beings are composed of approximately 70% water. Yet, more than 90% (i.e., test results evidence approximately 94%) are dehydrated. A person of average health absorbs less than 10% (i.e., 6-8% according to test results) of the water he or she drinks. Nearly 75% of all disease, from hypertension to strokes to cancer, depression, and arthritis, can be traced back to dehydration.

How well hydrated a person is affects every bodily process. Water transports all substances within the body. Water is the primary solvent for vitamins and minerals. A well-hydrated biological system enables various critical biological processes in humans, including the following: delivering nutrients to the cells; increasing blood oxygen levels; removing waste materials from the cells; and helping to remove toxic material from organs such as the liver and kidneys. Water is critical for the efficient function of energy generating cycles; provides electrical energy for brain function; is needed for the synthesis of neurotransmitters; is required for the production of hormones; and is necessary for all digestive functions. Proper consumption of water can reduce depression, stress, and anxiety; can restore normal sleep cycles; can increase the efficiency of the immune system; can reduce premenstrual syndrome (PMS) in females; helps to regulate ocular pressure; helps to regulate the adhesion index of blood cells; may reduce the risk of heart attacks and strokes; can prevent constipation; reduces the skin's signs of aging; aids in weight loss; increases joint flexibility and strength; and enhances athletic performance.

Figure 1:
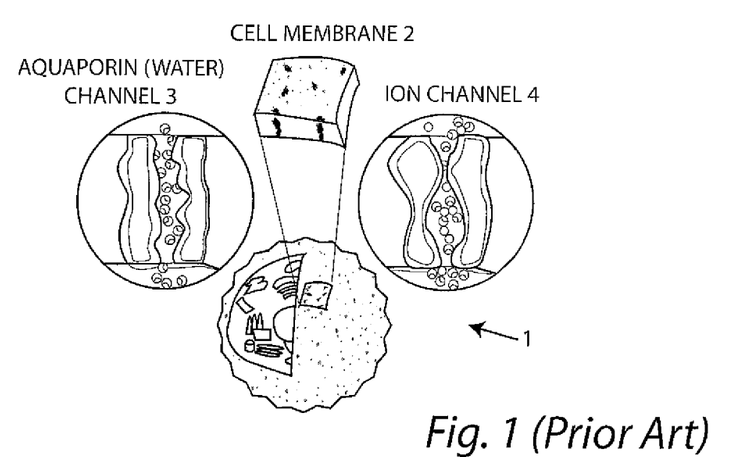
FIG. 1 is an illustration of how water and nutrients are transported into and out of cells.

Fundamentally, water is essential to the functioning of human cells. Considered in more detail:

"All living matter is made up of cells. A single human being has as many as the stars in a galaxy, about one hundred thousand million. The various cells—e.g. muscle cells, kidney cells and nerve cells—act together in an intricate system in each one of us." Swedish Academy of Science, Nobel Foundation In 2003, the Nobel Prize in Chemistry was awarded to two scientists whose discoveries clarified how water and salts (ions) are transported into and out of cells of the human body. Through these discoveries, Nobel Laureates Peter Agre and Roderick MacKinnon contributed to the fundamental chemical knowledge of how cells function to hydrate the tissue of an organism by demonstrating the way a human cell hydrates, one water molecule at a time. "They have opened our eyes to a fantastic family of molecular machines: channels, gates and valves all of which are needed for the cell to function." Swedish Academy of Science, Nobel Foundation. More particularly, as shown in FIG. 1, each cell 1 comprises a cell membrane 2 which comprises aquaporin channels 3 through which water is conveyed to and from the interior of the cell. Each cell 1 also comprises ion channels 4 that transport mineral ions into and out of the cell.

Hydration is a mathematical measurement of the fluid levels in the human body. The more hydrated the body is, the more efficiently the body transports nutrients and hormones and flushes toxins from cells.

The known prior art includes various devices and materials intended to enhance the properties of water. In the past, various techniques have been used that are intended to improve the biophysical properties of water. For example, two copper wires each having a length of 20.58 inches have been twisted together and joined at their ends to form a circular ring. A container of untreated water is then placed within the ring to treat the water. However, the treated water is not stable. As soon as the container is removed from within the ring, the beneficial properties of the treatment decrease substantially.

Additionally, Quantum Age Water marketed a product comprising volcanic soil containing pumice and minerals to which was added natural magnetite in a proportion of approximately 20% by weight. The mixture was then processed using psychic energy to enable the treatment of water to improve its biophysical properties.

In a third set of clinical trials on behalf of Quantum Age Water completed in December 2007, 12 microscopy subjects who drank water treated by stirring with an encapsulated formulation of material processed using psychic energy experienced an increase in blood oxygen (Blood $O^2$) from 88% to 95% in seven days and averaged a 10.25% increase in blood oxygen in 14 days. Also, 50 subjects averaged a 28.5% increase in hydration over baseline and a 22.5% margin over the placebo group within 30 days and averaged an 18.2% reduction in cellular toxins in 90 days with no measurable changes in toxin levels found in the control group.

The material processed using psychic energy was encapsulated in a sealed cavity disposed at one end of an elongated plastic stirrer whose stem is grasped by a person for stirring or was disposed in the space between two concentric tubes having a length of 18 to 24 inches and an approximate outside diameter of one-and-a-quarter inches for in-line installation in the plumbing of a water supply system or between smaller concentric tubes having a length of three to four inches for in-line installations such as in the supply line for an ice maker.

Unfortunately, it has been determined that the prior technique for processing the materials using psychic energy was not able to produce a product that was stable for a prolonged period of time. The processed material was found to lose approximately 20% of its water-treating energy in a period ranging from 16 to 18 months. The resulting dip in energy has been found unacceptable for a commercial product and most commercial applications.

There are thus shortcomings to the above and other known devices and techniques for improving the biophysical properties of water. Yet, proper hydration is critical to every bodily function. However, medical science has heretofore not been able to create a natural sustainable solution for raising levels of hydration, oxygenation, and cellular detoxification for an extended period of time.

In view of the shortcomings of known devices and techniques, certain examples in accordance with the present invention provide a product-by-process and encapsulation devices for the resulting product that transform untreated water to a nearly perfect balance for assimilation by a human cell through a natural non-invasive technology. Furthermore, various examples of the present invention provide improved encapsulation devices and treatment methods for use of the product of the character described which may be manufactured at low cost and used for other commercial applications.

SUMMARY OF THE INVENTION

The water treatment products-by-process in accordance with various examples of the present invention consist of one of a plurality of processed formulations of minerals comprising mica and magnetite processed in accordance with the examples of the present invention. As demonstrated by data obtained during human clinical tests, the efficacy of water treated using the processed formulations of minerals relates generally to the treatment of potable water suitable for human consumption. However, not only the chemistry of potable water, but also the chemistry of non-potable water may be balanced by treatment, as well, thereby improving the biophysical properties of such water for uses other than for consumption by humans, such as for pretreatment of water prior to purification for human consumption, waste treatment, agriculture, horticulture, aquaculture, animal husbandry, medical use, and the like.

Various examples of encapsulation devices for containing the water treatment product and methods are also provided in accordance with the present invention for treatment of potable water suitable for human consumption, as well as for other uses. Different blends of minerals affect the amount of coherent energy emitted by each example, the unique enhancing biophysical benefits of each for human use, and, hence, the recommended time of day for use. For example, a first example is preferably provided for basic 24/7 use by a person day or night. The first example is intended for everyday use to enhance hydration, oxygenation, and detoxification and to promote stress relief. A second example is preferably provided for daytime use by a person. The second example is intended for optimizing athletic performance. A third example is preferably provided for use by a person after work hours or exercise. The third example is intended for promoting calmness, relaxation, meditation, use during soothing baths, or the like. A fourth example is preferably provided for daytime use by a person. The fourth example is intended for opening the heart chakra. A fifth example is preferably also provided for daytime use by a person. The fifth example is intended for emotional grounding, stabilizing, and strengthening. A sixth example is also preferably provided for daytime use by a person. The sixth example is intended for stimulating mental clarity, focus, and inspiration. A seventh example is preferably provided for use with food or drink to be consumed by a person. The seventh example is intended for enhancing the flavors in food when placed in or near the food for approximately one minute or more, or beverages such as inexpensive wines stirred to taste. By way of a further example, an eighth example is preferably provided for horticultural and aquacultural use. The eighth example is intended for enhancing the vitality of house and garden plants, as well as fresh produce. The eighth example also increases the available oxygen for fish and plant life in fresh or saltwater aquariums and ponds not exceeding 500 gallons; but the amount of the mineral blend can be increased to treat greater volumes of water for such uses.

All example and methods used for potable water for human consumption are hydrating, oxygenating, and detoxifying, as validated through human clinical tests over a 90-day period involving hundreds of persons, using FDA approved testing procedures. For example, these clinical tests have demonstrated hydration of approximately five times more than by simply drinking purified water, an increase in blood oxygen level by more than 10%, an increase in energy level, or adenosine tri-phosphate (ATP), by approximately 11.1%, and cellular detoxification of more than 18.8%. Clinical test subjects consequently experienced more energy, enhanced athletic performance, reduced cellular toxins and weight loss, greater nutrient absorption, a healthier immune system, relief from headaches and joint pain, and younger looking skin, hair, and nails, as well as more restful sleep.

In the use of one example of encapsulation device, a person places the mineral end of the encapsulation device in a container of untreated water, for example, a glass of potable water, for approximately 20 to 30 seconds or longer for a larger volume container having a volume of a gallon or less and stirs, or simply places the mineral end in the water without stirring. Longer treatments do not over-energize the water or affect the useful life of the encapsulated minerals. The example can also be used to treat water intended for other uses such as in washing machines, baths, pools, spas, fish tanks, ponds, and the like, if simply deployed in the water being treated.

The foregoing and other objects, features, and advantages of the present invention will become more readily apparent from the following detailed description of various examples, which proceeds with reference to the accompanying drawing.

BRIEF DESCRIPTION OF THE DRAWING

The various examples of the present invention will be described in conjunction with the accompanying figures of the drawing to facilitate an understanding of the present invention. In the figures, like reference numerals refer to like elements. In the drawing.

DETAILED DESCRIPTION OF THE PREFERRED EXAMPLES

Figure 2:
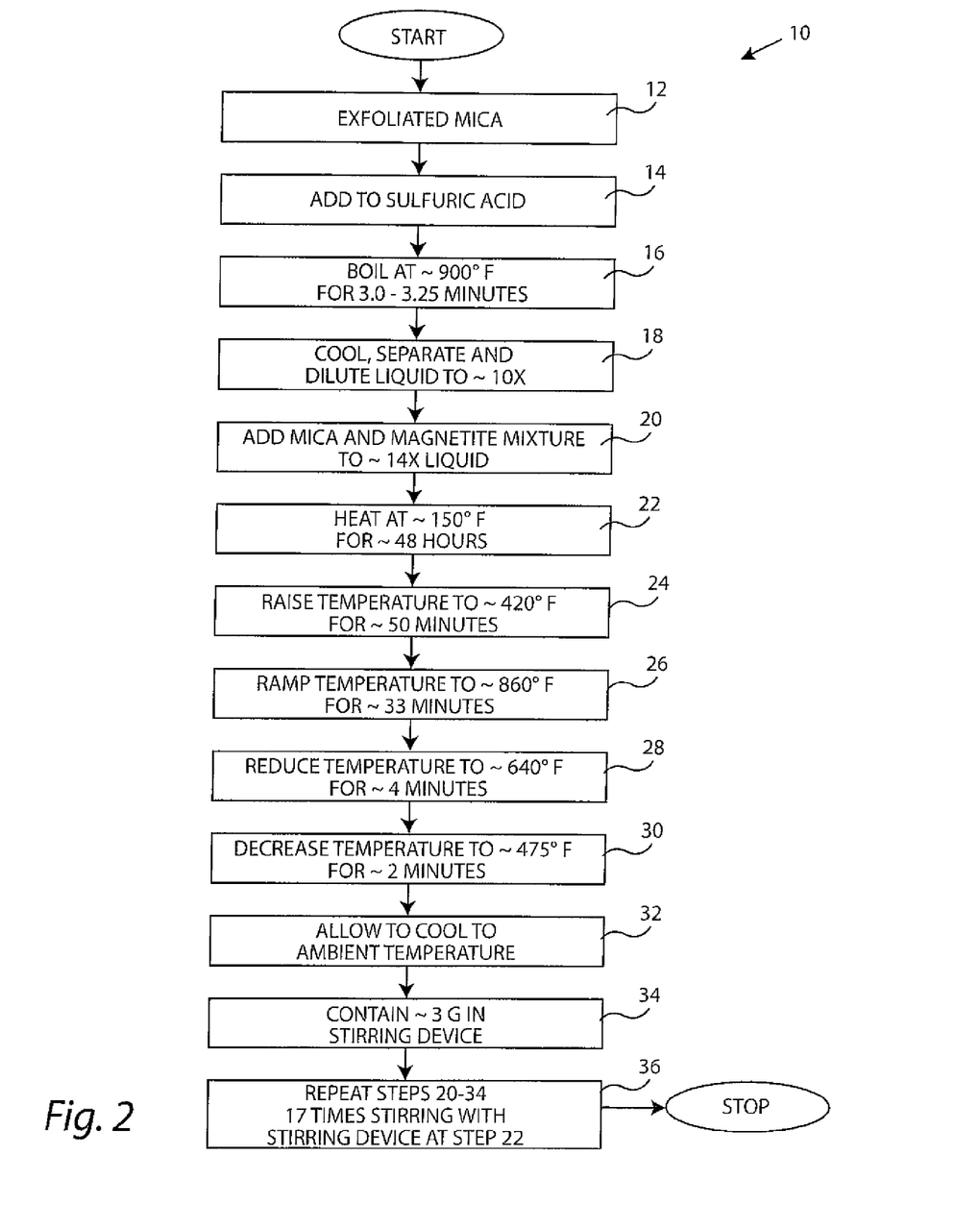
FIG. 2 is a flow diagram illustrating the process for producing a water treating product in accordance with an example of the present invention.

In accordance with one aspect of the present invention, a product is produced which can be used to balance the chemistry of water to improve the hydration, oxygenation, and detoxification properties of the water. One example of a process for producing the product is shown in FIG. 2, generally indicated by the numeral 10. In accordance with one example, the product comprises mica, preferably black mica.

A first step 12 for producing the product includes obtaining starting material comprising mica, preferably black mica. Black mica, i.e., biotite, is an iron-rich (mafic) silicate material that also typically contains other minerals.

In one example, the mica that constitutes the starting material is exfoliated mica, for example, commercially available exfoliated granular black mica, which has been dried such as by having been heated to 2,200° F. to substantially remove moisture. In an alternative example, kyanite, which is another form of mica, can be used as the starting material. Other starting materials in the form of mica are also contemplated.

Granular black mica is commonly commercially available in a 40 mesh (420 microns) size. In one example, it has been found preferable to grind the black mica, for example, using a mortar and pestle, to reduce the granular size to an approximately 50 mesh (297 microns) size.

In the next step, indicated by a step 14 shown in FIG. 2, the mica is added to food grade sulfuric acid ($H_2SO_4$) in the preferred ratio of 1 gram of 50 mesh mica to 5 ml of sulfuric acid. In a preferred example, approximately 1.5 liters of sulfuric acid may be placed in a 12-inch fused quartz or borosilicate beaker or flask, and then 300 grams of the mica are added to the beaker or flask and heated to approximately 900° F. (the approximate boiling point of the sulfuric acid), as indicated by a step 16 shown in FIG. 2. Accordingly, the beaker or flask is preferably set on a hot plate, the sulfuric acid is poured into the beaker or flask, the mica is added to the acid, and heat is then applied using the hot plate until the temperature of the mixture reaches 886-887° F. In one preferred example, the mixture is boiled for approximately 3.0 to 3.25 minutes. The result is that the minerals are boiled out of the mica.

Then, in a step 18 shown in FIG. 2, the liquor resulting from the boiling is cooled, separated, and diluted from its original concentration (200×) to a diluted concentration on the order of approximately 10× and preferably 13×-14× by adding pure distilled water.

Thereafter, in a preferred example, a mica/magnetite mixture is then formulated in a step 20 shown in FIG. 2. Although black mica has a relatively high iron content, in one preferred example, approximately 1.0% percent by weight of natural magnetite ($Fe_3O_4$) is added to fresh mica. The magnetite in a proportion of approximately 1.0% by weight is preferably mixed with the mica, as indicated by the step 20, to increase the iron content to between 60 and 2,200 ppm. The lower portion of the range of iron content is sufficient for effective water treatment; while the higher portion of the range is more suitable to enhancing results in the treatment of other water-based substances such as blood. In a preferred example, 1.8 grams of magnetite is added to 100 grams of black mica. In the preferred example, powdered magnetite having a mesh size of approximately 200 mesh (74 microns) size is thoroughly admixed with the mica, for example, by sifting or shaking.

The mica/magnetite mixture is preferably added to approximately 14× concentrate liquid and preferably to 13.75× concentrate liquid in the approximate ratio of 1 gram of mica/magnetite mixture to 5 ml of 13.75× concentrate, as indicated by the step 20 shown in FIG. 2. For example, 500 ml of 13.75× concentrate liquid is placed in an open beaker or flask, and 100 grams of mica/magnetite mixture is added. As indicated by a step 22 shown in FIG. 2, the beaker or flask containing the mixture is then stirred and heated for approximately 48 hours maintaining a constant temperature of approximately 150° F. preferably using a full-spectrum heat lamp.

Next, the mixture is placed in a furnace, and the temperature is slowly raised to approximately 420° F. and maintained for a period of approximately 50 minutes, as indicated by a step 24 shown in FIG. 2. After the target temperature is reached, the temperature is ramped to approximately 860° F. for a period of approximately 33 minutes, as indicated by a step 26 shown in FIG. 2. Next, as indicated by a step 28 shown in FIG. 2, the temperature is reduced to approximately 640° F. for approximately four minutes. Then, the temperature is further decreased to approximately 475° F. for approximately two minutes, as indicated by a step 30 shown in FIG. 2. As indicated by a step 32 shown in FIG. 2, the mixture is allowed to cool to ambient temperature.

Approximately 3.0 grams of the cooled mixture constituting an intermediate byproduct is then placed in a sealed stirring device, as indicated by a step 34 shown in FIG. 2. Then, the process beginning at the step 20 with the use of the approximately 14× liquid concentrate is repeated, as indicated by a step 36 shown in FIG. 2. That is, new mica/magnetite mixture is preferably added to 13.75× concentrate liquid in the approximate ratio of 1 gram of mica/magnetite mixture to 5 ml of 13.75× concentrate (step 20). For example, 500 ml of 13.75× concentrate liquid is placed in an open beaker, and 100 grams of mica/magnetite mixture is added. The beaker containing the mixture is then heated for approximately 48 hours maintaining a constant temperature of approximately 150° F. preferably using the full-spectrum heat lamp (step 22), but this time while stirring with the sealed stirring device containing the intermediate byproduct produced during the preceding series of steps (at step 34).

Next, the mixture is placed in the furnace, and the temperature is slowly raised to approximately 420° F. and maintained for a period of approximately 50 minutes (step 24). After the target temperature is reached, the temperature is ramped to approximately 860° F. for a period of approximately 33 minutes (step 26). Next, the temperature is reduced to approximately 640° F. for approximately four minutes (step 28). Then, the temperature is further decreased to approximately 475° F. for approximately two minutes (step 30). The mixture is then allowed to cool to ambient temperature (step 32).

The result is a second intermediate byproduct mixture, which is placed in a sealed stirring device (step 34), and the process beginning at step 20 with the use of the approximately 14× liquid concentrate is repeated, using the stirring device containing the second intermediate byproduct for stirring the mixture being heated for approximately 48 hours maintaining a constant temperature of approximately 150° F. preferably using the full-spectrum heat lamp when repeating step 22. In one example, the process beginning with step 20 is then repeated another 16 times, for a total of 18 repetitions, each time using a stirring device containing the intermediate byproduct mixture produced during the immediately preceding series of steps at step 34.

The product for treating water is produced at the conclusion of the seventeenth repetition of the series of steps beginning at step 20 with the use of a fresh mica/magnetite mixture and approximately 14× liquid concentrate and using the stirring device containing the intermediate byproduct from the seventeenth repetition for stirring the mixture being heated for approximately 48 hours maintaining a constant temperature of approximately 150° F. preferably using the full-spectrum heat lamp. That is, the product for treating water is complete after performing the sequence of steps 20-34 a total of 18 times, but using the stirring device resulting from repeating the step 34 for stirring each time step 22 is repeated 17 times. Furthermore, additional product for treating water can subsequently be produced directly by skipping steps 14 to 18 and simply repeating steps 20 to 32, reusing the stirring device containing the intermediate byproduct from the seventeenth repetition during step 22.

Water can be tested for energy by measuring the milliwatts (coherent energy) and millivolts of a sample of water. The end product produced by the process in accordance with the example shown in FIG. 2 brought 90-day test water from 90 milliwatts up to 9,994 milliwatts, while reducing the millivolts from 88 to 56, within approximately 30 seconds of exposure to the end product. Additionally, tests have demonstrated that the end product has stabilized the surface tension of treated water at approximately 62, which is conducive to the integrity of cellular transport of water molecules. The end product lowers the specific gravity of untreated potable water from about 1.011 to 1.023 to below the threshold of 1.009 to approximately 1.002 to 1.003, more closely approaching the ideal specific gravity for water of 1.000, as well as provides improved water resistivity from 10 to 167 ohm-meters. Tests have also demonstrated that exposure to the end product stabilizes the pH of treated potable water (typically 5.5 to 7.0 pH, including purified water adjusted to a pH of 7.0 by the addition of minerals), and that the treated water will remain more than 99% stable in an open container for at least 48 hours and more than 95% stable in a sealed container for a minimum of three months. Consequently, exposure to the end product provides a natural sustainable solution for raising levels of hydration, oxygenation, and cellular detoxification.

In accordance with various additional examples of the present invention, various other materials may be added to the end product produced by the process in accordance with the example shown in FIG. 2 for treating water intended for human consumption to provide enhanced properties. In one example, white Brazilian quartz crystal may be added in an approximate ratio of one gram of white Brazilian quartz to one to three grams of end product, resulting in a formulation that is approximately 25-33% by weight white Brazilian quartz. This formulation provides higher energy. In one alternative example, rose quartz and white Brazilian quartz can be used as additives to the end product in an approximate ratio of 0.25 gram of rose quartz to 0.25 gram of white Brazilian quartz to 2.5 grams of end product to enhance opening of the heart chakra. In a second alternative example, amethyst and white Brazilian quartz can be added to the end product in an approximate ratio of 0.25 gram of amethyst to 0.25 gram of white Brazilian quartz to 2.5 grams of end product to provide a claming effect useful for alleviating insomnia. In a third alternative example, reishi mushroom, amethyst, and white Brazilian quartz can be used as additives to the end product in an approximate ratio of 0.6 gram of reishi mushroom to 0.25 gram of amethyst to 0.25 gram of white Brazilian quartz to 2.6 grams of end product to produce a meditative relaxed state. In a fourth alternative example, lion's mane mushroom and white Brazilian quartz can be added to the end product in an approximate ratio of 0.5 gram of lion's mane mushroom to 0.25 gram of white Brazilian quartz to 2.65 grams of end product to improve mental acuity and clarity. In a fifth alternative example, Kunzite crystal found in Pakistan and Afghanistan and white Brazilian quartz can be used as additives to the end product in an approximate ratio of 0.5 gram of Kunzite crystal to 0.25 gram of white Brazilian quartz to 2.55 grams of end product to provide a relaxing effect useful for countering autism. In a seventh alternative example, obsidian and white Brazilian quartz can be added to the end product in an approximate ratio of 0.25 gram of obsidian to 0.25 gram of white Brazilian quartz to 2.8 grams of end product for improved grounding. In an eighth alternative example, tourmaline and white Brazilian quartz can be used as additives to the end product in an approximate ratio of 0.25 gram of tourmaline to 0.5 gram of white Brazilian quartz to 2.55 grams of end product to improve energy.

In another example, an additive can be mixed with the end product for agricultural use. Preferably, an approximate ratio of 0.1 to 0.3 grams of SuperCer-C Ceramic Powder commercially available from Sustainable Community Development LLC located in Kansas City, Mo. can be added to 3.0 grams of end product to treat water to promote healthy plant root growth and nutrient-rich soil.

Figure 3:
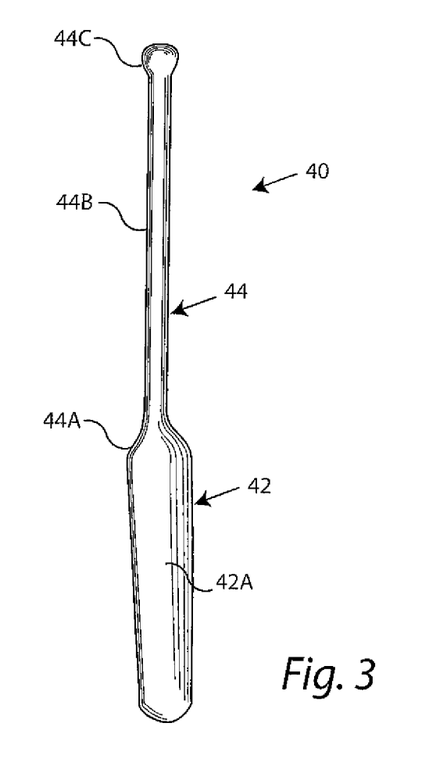
FIG. 3 is an isometric view illustrating an example of a product encapsulation device in accordance with the present invention.

In accordance with another aspect of the present invention, various encapsulation devices for the product produced by the process described in conjunction with the example shown in FIG. 2 are provided. For example, as shown in FIG. 3, an encapsulation device 40 comprises a slightly tapering cylindrical mineral containing end 42 having an internal cavity or reservoir 42A for containing approximately 2.75 to 3.0 grams of the product for treating water. The encapsulation device 40 also comprises a stem 44. The stem 44 comprises a first end 44A in the form of a cap that interfits with the mineral containing end 42 and seals the water treating product within the mineral containing end. The stem 44 further comprises a shaft 44B which can be grasped by a person's hand to stir or place the encapsulation device 40 in a container of untreated water to treat the water. Preferably, the stem 44 also comprises a knob end 44C.

Figure 4:
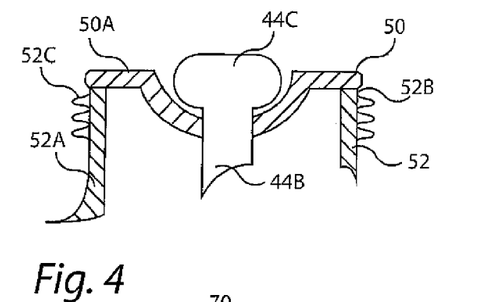
FIG. 4 is a partial cutaway view of a gasket for maintaining the encapsulation device shown in FIG. 3 in the neck of a container for treating the contained water.

Various accessories may be used in combination with the encapsulation device 40. For example, as shown in FIG. 4, a gasket 50 can be slid over the knob end 44C of the encapsulation device 40 with the shaft 44B of the encapsulation device extending through the gasket. The gasket 50 enables the encapsulation device 40 to be suspended within the neck 52A of a bottle 52 containing untreated water or an untreated water-based beverage or other water-based liquid. The gasket 50 also preferably comprises a flange 50A that forms a seal between the lip 52B of the neck 52A of the bottle 52 and a threaded bottle cap (not shown) that may be engaged with threads 52C provided on the neck of the bottle to seal the bottle while the encapsulation device 40 is suspended within the bottle.

Figure 5:
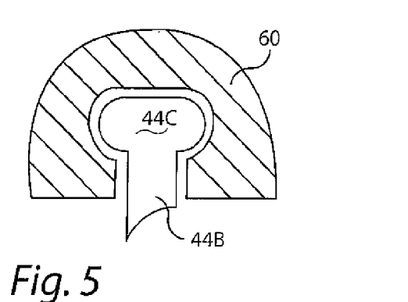
FIG. 5 is a partial cutaway view of a flotation cap for aiding flotation of the encapsulation device shown in FIG. 3 in a volume of water for treating the water.

Additionally, as shown in FIG. 5, a flotation cap 60 can be slid onto the knob end 44C of the encapsulation device 40 with the shaft 44B of the encapsulation device extending out of the flotation cap. The flotation cap 60 enables the encapsulation device 40 to float in a volume of untreated water or an untreated water-based liquid. The flotation cap 60 enables the encapsulation device to treat larger volumes.

Figure 6:
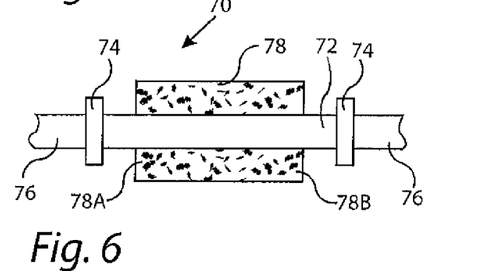
FIG. 6 is a partial cutaway view of a product encapsulation device in accordance with a second example of the present invention for treating flowing water from a water supply.

FIG. 6 is a partial cutaway view that shows an encapsulation device 70 intended to be installed in a water supply line, for example, to connect a water supply to the plumbing of a building such as a residence, business, or industrial facility to supply water to the structure or facility. The encapsulation device 70 comprises a cylindrical first or inner tube 72 which is attached by couplings 74 in line with the water supply line 76 through which untreated water is introduced. The inner tube 72 may be 18-24 inches in length and have a first diameter, for example, one inch. The encapsulation device 70 further comprises a cylindrical second or outer tube 78 shorter than the first tube 72 and having a larger second diameter, for example, 1.25-1.5 inches, concentrically disposed with respect to the first tube. A predetermined amount of the water treating product is deposited in the interstitial region between the first and second tubes 72, 78, and then the space between the first tube and the second tube at the respective ends 78A and 78B of the shorter second tube are sealed, for example, by means of epoxy, to retain the water treating product. The encapsulation device 70 can alternatively be inserted in a pipeline connected to a water supply to produce bottled treated water for human consumption, in a water supply line to provide treated water for agriculture (e.g., water to be sprayed onto crops, dripped or flowed onto soil or sand in which crops are grown, or used for hydroponic cultivation) or for aquaculture, or even in a sewer line to aid sewage treatment. In one contemplated modification, the encapsulation device 70 may be increased in size and installed at the output of a water filtration plant for supply of bulk treated water to the public. In another contemplated modification, the encapsulation device 70 may alternatively be reduced in size, for example, the first tube 72 may have a diameter of one-eighth inch and a length of 3.0-4.0 inches, and the second tube 78 may have a diameter of one-quarter inch and a shorter length than the first tube, which may then be inserted in line in an ice maker water supply line or inlet line of an aquarium filtration system, for example. In a further contemplated example, the encapsulation device 70 may be provided with only a single coupling 74 sized to connect to a garden hose and configured as a hose extension to water plants with treated water.

Alternatively, the product produced by the process described in conjunction with the example shown in FIG. 2 can be distributed throughout a supporting or binding material. For example, the product can be adhesively applied to sheet material such as plastic or fiberglass that can be wrapped around a structure through which water to be treated is supplied such as a water supply line for a residence, business, or industrial facility and thereafter covered with insulation. Also, the water treating product can be dispersed and suspended in a coating material such as paint applied to a water supply line and thereafter covered with insulation.

Figure 7:
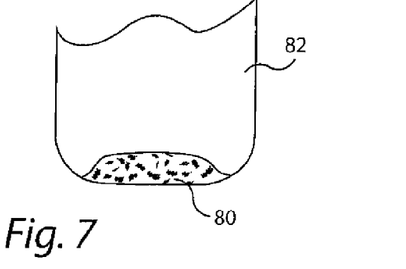
FIG. 7 is a partial cross-sectional view of a product encapsulation device in accordance with a third example of the present invention for treating water in a container.
Figure 8:
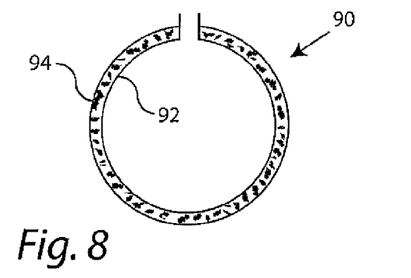
FIG. 8 is a partial cross-sectional view of a product encapsulation device in accordance with a fourth example of the present invention for treating water in a double-walled container.

In another example, the product produced by the process in accordance with the example shown in FIG. 2 may be integrated within the structure of a container for water or a water-based beverage or other water-based liquid. For example, as shown in FIG. 7, a reservoir 80 of water treating product may be provided in the bottom of a container 82 such as a molded plastic container for storing water or a water containing beverage. In one contemplated modification, a reservoir 80 of water treating product may be provided in the bottom of a pet water bowl containing water for consumption by a pet. In another example, the product for treating water may be retained between an inner wall 92 and an outer wall 94 of a canteen 90, as shown in FIG. 8, or between the walls of other double-walled containers for water or a water containing beverage or other water containing substance.

Figure 9:
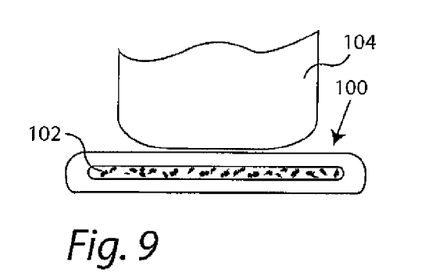
FIG. 9 is a partial cross-sectional view of a product encapsulation device in accordance with a fifth example of the present invention for treating water in a container placed thereon.

In yet another example, a reservoir 102 of the product produced by the process described in conjunction with the example shown in FIG. 2 may be integrated within the structure of a coaster or trivet 100 on which is placed a container 104 of water or water containing substance, as shown in FIG. 9.

Figure 10:
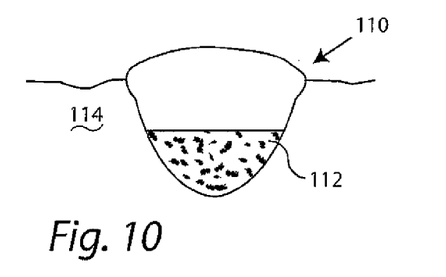
FIG. 10 is a partial cross-sectional view of a product encapsulation device in accordance with a sixth example of the present invention for treating large volumes of water.

In a further example, as shown in FIG. 10, a reservoir 112 of the product produced by the process described in conjunction with the example shown in FIG. 2 may be integrated within the structure of a flotation device 110 to treat a body of water such as a pond 114 or in a smaller size flotation device to treat a smaller volume of water, for example, a flotation device configured for an aquarium or configured as a toilet tank drop-in.

Figure 11:
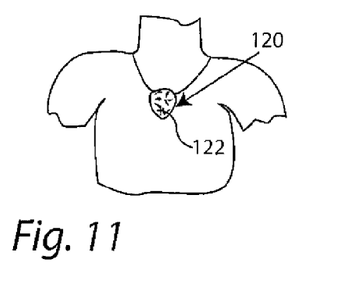
FIG. 11 is a partial cutaway view of a product encapsulation device in accordance with a seventh example of the present invention worn on the human body for therapeutic purposes.

Other contemplated uses include producing potential therapeutic effects by locating a reservoir of the product produced by the process described in conjunction with the example shown in FIG. 2 in close proximity to the body of a person. For example, as shown in FIG. 11, a reservoir 122 of the product can be integrated into a pendent 120 or other jewelry worn on the body. In other contemplated therapeutic examples, the product can be integrated into the lining of clothing or embedded in a sleep mask or other article intended to be worn on a person's body.

Still other contemplated uses include the treatment of water or water-based liquids using the product produced by the process described in conjunction with the example shown in FIG. 2 to reduce the amount of surfactants needed in the use of products such as shampoo, detergents, and the like. Also, adding the product produced by the process described in conjunction with the example shown in FIG. 2 to a coating applied to the hull of a watercraft may reduce drag in the water. Consequently, the product can be employed for a myriad of additional commercial uses.

The materials of construction of the various encapsulation devices shown in FIGS. 3 and 6-11 may be varied to suit the requirements of any specific encapsulation device. The parts shown in the drawing figures may be constructed of any available plastic substances in molded or extruded form or metal such as copper, aluminum, or stainless steel, ceramic, glass, or one of various polymers.

There are numerous uses for water treated with the product produced by the process described in conjunction with the example shown in FIG. 2 employing one or more of the encapsulation devices shown in FIG. 3 or 6-11. One use is bottled water for human consumption. For example, bottled water can be produced by flowing water through the encapsulation device 70 shown in FIG. 6 installed at a bottling factory and distributed in containers. Sterile saline and medical/pharmaceutical water may be similarly treated at a bottling facility prior to being sealed in a container. In one contemplated modification, a water-based beverage such as a sports drink can be produced comprising treated water and preferably further comprising additives based on metabolic formulae (which may be either mixed with the treated water or supplied in packets to be added to treated water by users)

for increased ATP and athletic performance and recovery for use by persons who engage in physical fitness exercise, as well as amateur and professional athletes. These sports drinks may also be distributed in containers. Flavoring such as natural fruit flavors, for example, essence of orange, lemon, lime, or berry can also be added to the treated water.

An additionally contemplated use of treated water is for weight loss. Persons typically carry excess weight due to the presence of toxins encapsulated in fat in their dehydrated bodies. Using treated water hydrates and cleanses toxins from a person's body, and fat may be reduced as the body eliminates toxins.

Substantial testing shows that the water treating product balances and stabilizes the chemistry in virtually any potable water. The product works effectively, naturally, quickly, and inexpensively. Stabilization tests demonstrate that treated water remains more than 99.0% stable for a minimum of 48 hours in an open container, and retains more than 95.0% of the initial chemical balance of treated water for a minimum of three months in a sealed container.

As verified by human clinical testing, water treated by the end product-by-process in accordance with one example of the present invention raises all three of the critical health factors of hydration, oxygenation, and detoxification to therapeutic levels, by a person simply drinking the standard daily recommended amount of water, which is half one's body weight in ounces, for example, when the product is encapsulated and used to stir untreated water for approximately 20-30 seconds prior to consumption. The water treating product is preferably encased in a container made from surgical instrument grade polymers. Continued use will maintain these therapeutic levels, consistently saturating cells with oxygenated water to optimize the action of the body's many regulatory and cleansing systems.

Furthermore, human clinical tests have proven that drinking water balanced naturally by the water treating product for optimally hydrating human cells is as vital a source of oxygen for human cells as is breathing oxygen through the lungs. In connection with the human clinical tests, to determine the recommended amount in ounces of water to consume daily, a person's body weight is divided in half, such that a person should drink approximately one half of his or her weight in ounces per day. Nevertheless, of more than 50,000 persons involved in various human clinical studies performed over 10 years by Fenestra Research Labs located in Las Vegas, Nev., although drinking the recommended amount of untreated water, 94% were found to still be dehydrated. In contrast, drinking the recommended daily amount of water treated by the product produced by the process described in conjunction with the example shown in FIG. 2 increased hydration quickly and dramatically. The required balance of water chemistry that accomplishes the above criteria of hydrating and oxygenating human cells with single water molecules flowing freely into the cells has been verified through water analysis research and hydration testing by Melonie Montgomery of Fenestra Research Labs.

Considered in more detail, Fenestra Research Labs most recently conducted a human clinical trial for evaluating the safety and efficacy of water treated with the product produced by the process described in conjunction with the example shown in FIG. 2 in a randomized, placebo controlled study in the Spring of 2010. The purpose of this human clinical study was to evaluate the ability of water treated with the product to improve cellular hydration and blood oxygen levels. The direct objective of this investigation was to evaluate the performance of water treated by the test product compared to a placebo (tap water) in improving/increasing hydration and blood oxygen levels at the cellular level.

This was a 90-day, 125-subject (58 women and 67 men) study using subjects drawn from a large population of people in generally good health, but evidencing dehydration. Subjects were adults 18 years old or older. Following an initial screening at Visit 1 (week 0), subjects entered a 1-week baseline period (subjects were told to refrain from taking any unnecessary over-the-counter medications, prescription drugs, or natural products for the remainder of the study). Subjects who met all inclusion criteria and none of the exclusion criteria during the intake at Visit 2 (week 1) were then provided either the placebo (tap water) or were provided purified water adjusted to a 7.0 pH by the addition of minerals and the product produced by the process described in conjunction with the example shown in FIG. 2 encapsulated in the encapsulation device 40, along with a protocol describing daily dosing amounts and kinds of water to be consumed exclusively. The second evaluation on Visit 3 (week 3) was performed following standard procedures, and the study's protocol was explained to each subject on an individual basis. Evaluations of test subjects were completed on Visit 4 (week 5), on Visit 5 (week 9), and the final testing was done on Visit 6 (week 14) of the trial.

The subjects were randomized into two groups and drank either the placebo (tap water) or treated water produced by treatment of 7.0 pH purified water with the product produced by the process described in conjunction with the example shown in FIG. 2. Each subject was provided enough water for him or her to drink one-half of his or her body weight in ounces daily. Those provided with the encapsulation device 40 containing the water treating product were instructed to use the device as a stir stick to stir a 10-ounce glass of the purified water for 30 seconds, and then to consume the treated water. Each subject was instructed that he or she was only to consume his or her specific water and under no circumstances was he or she to drink any other water product alone or in any water mixed product. All subjects were instructed to make no changes to their daily food consumption in regards to the amount or the types of food they were consuming daily. Compliance was monitored and maintained through bi-weekly telephone calls.

Additionally, 25 randomized subjects had arterial blood drawn for the purpose of measuring oxygen saturation through standard laboratory practices. Each blood draw was performed from the lower part of either the right or left arm. Each draw was collected in three separate red-top vials on each draw occasion. The single reported measurement of each office visit is an average of the three blood draws and their data. Blood draws were done exclusively on these 25 subjects each time they were seen during the study.

During testing the flowing parameters were measured using standard equipment: 1) heart rate; 2) blood pressure; 3) respiration; 4) pulse; 5) oxygen saturation; and 6) Optimal Wellness Test parameters. The analyses comprising the Optimal Wellness Test are set forth in Table 1, below.

TABLE 1

| Test | Urine | Blood |
|---|---|---|
| pH | X | X |
| rH2 (oxidation and reduction) | X | X |
| r (resistivity) | X | X |
| C (conductivity) | X | X |
| Nitrate | X | X |

TABLE 1-continued

| Test | Urine | Blood |
| --- | --- | --- |
| Ammonia | X | X |
| Brix (refractometry) | X | |
| Specific Gravity | X | X |
| Oxidative Stress | X | X |
| Cellular Respiration | X | X |
| Renal Balance | X | X |
| Hepatic Balance | X | X |
| Digestion | X | X |
| Hydration | X | X |
| Toxicity | X | X |
| Adrenal Balance | X | X |
| Protein digestion | X | X |
| Carbohydrate digestion | X | X |
| Blood Sugar Balance | X | X |
| Anabolic State | X | X |
| Catabolic State | X | X |
| Surface Tension | X | X |

There are four Optimal Wellness Test parameters used to determine overall hydration: a) conductivity; b) resistivity; c) surface tension; and d) specific gravity. Determination of hydration involves a mathematical formula developed by Fenestra Research Labs based on four parameters (conductivity, resistivity, surface tension, and specific gravity) to assess whether or not a person is moving towards or is within the wellness range. The more a person is outside the range for hydration wellness, the more dehydrated he or she is considered to be. To measure the four parameters for computation of cellular hydration, it is preferred to analyze saliva and urine samples from the person's body.

The foundation for evaluating the electrical properties in the Optimal Wellness Test is the basic formula for electrical resistivity ρ defined by, $$\rho = \frac{E}{J}$$

where
ρ is the static resistivity (measured in ohm-meters, Ω-m)
E is the magnitude of the electric field (measured in volts per meter, V/m); and
J is the magnitude of the current density (measured in amperes per square meter, $A/m^2$).

Conductivity is the reciprocal (inverse) of electrical resistivity, ρ, and has the SI units of siemens per meter ($S \cdot m^{-1}$) and CGSE units of inverse second ($s^{-1}$):

$$\sigma = \frac{1}{\rho}.$$

Through the interplay of voltage with both conductivity and resistivity, basic knowledge about intra- and extracellular hydration can be assessed. Conductivity is related to intracellular hydration, and resistivity is related to extracellular hydration. Conductivity is a measurement of the amount and quality of electrical current in the body. Salts are electrolytes, and they are responsible for the electrical conduction of information in the body. Conductivity is the measurement of the quantity of current flow within the biological specimen and is an indicator of osmotic pressure, heat loss, and fluid balance. If the current in the body is too high or too low, there will be symptoms of degeneration of the body. Resistivity reflects the flow of ions across cellular membranes. The resistivity is the measurement of the relative concentrations of minerals contained within the test sample. The slight difference in the concentration of minerals found in the plasma versus the amount found inside the cells creates a voltage gradient called the membrane potential. Therefore, resistivity is a direct reflection of the body's ability to conduct electrical currents. With the fluid samples obtained from each person in the study, these parameters can be measured and evaluated.

Specific gravity and surface tension pertain more to chemical properties, but also relate to electrical properties of the body. Surface tension is directly related to inward molecular attraction, with the obvious implication that if solids are suspended properly via molecular combinations with $H_2O$, then the fluids of the body will have lower surface tension. The specific gravity of any given bodily fluid reveals the content of solids in solution, with higher and higher concentrations of solids, both intra- and extracellular, raising the specific gravity number as a possible indicator of dehydration.

Mathematically, specific gravity is similar to density. Specific gravity is defined as density of a substance divided by the density of water. Since the units will cancel out in any computation, it simply means that the only difference between specific gravity and density is that the there are no units associated with specific gravity, as is the case with density. With bodily fluids, density is a function of the types and amounts of solids found in solution. The more there are of substances in solution that are heavier than water, the higher the density will be. With dehydration, whether it is intra- or extracellular, the density of fluids will be higher because the water content decreases as the solids content increases. The converse is true for increased hydration. The surface tension of fluids in the body can be compared through technological analysis with that of pure water. Higher surface tension implies a decreased capacity for cellular permeability for any given fluid. Surface tension of a fluid can be defined as inward molecular attraction forces, which must be overcome to increase the surface area. Surface tension is the energy required to increase the surface area of a liquid by a unit amount. In water, the intermolecular hydrogen bonds are involved in the inward attraction forces. The surface tension of water at 20° Centigrade is $7.29 \times 10^{-2}$ $J/m^2$.

Toxicity is an assessment of what the body is containing too much of, causing a toxic relationship between the substance and the cellular body. There are several different mathematical representations of ammoniums, nitrates, salts, oxygen, ureas, and other toxic materials that may be present in the body. Significant changes in toxicity have not been observed in studies less than three months in duration. The nitrate and ammonium particles in the body are the result of poor digestion. For the liver to make energy, the liver incites the urea cycle to occur. The body cannot use amino acids that have not been digested properly. Another cause of ammonium production is bacterial metabolism in the intestinal lumen. This released ammonium is absorbed and transported to the liver. The liver treats the nitrates and ammoniums as toxins, because poor digestion has rendered the byproduct unusable. This unusable material is converted into urea and stored in the body. Urea can only be stored for 72 hours before it becomes toxic, by which time the urea must be broken down to urea salts of nitrate and ammonium nitrogen. The numbers for perfect digestion are 3 for nitrate and 3 for ammonium. Both nitrates and ammoniums numbers influence the electromagnetic condition of body fluids. Together they determine the amount of energy being lost from the system. Nitrate and ammonium are related to digestion, and they provide a snapshot of the amount of usable energy being produced by digestion. The chemical reaction that takes place between food and digestive enzymes is vital to wellness. The correct balance of water, calcium, and oxygen in the body is necessary for usable energy to result.

Additionally, the study tested for the amount of certain heavy metals in the body. The heavy metals tested for were: a) mercury; b) lead; 3) cadmium; 4) aluminum; and 5) nickel.

In the study, both groups of test subjects had an average hydration saturation number of six percent at the time of baseline testing. This number of six percent is a representation. It appears through extensive hydration studies (61 to date) conducted by Fenestra Research Labs that perfect hydration occurs between 30%-50% cellular hydration levels. There are several other factors that also must be optimal or within range for this to make a significant change in cellular functions. These other factors are pH, ORP (redox potential), and toxicity indicators.

Certain physiologic parameters indicative of various states of toxicity, oxidative stress, and hydration were measured during the study using Optimal Wellness Test apparatus and calculation algorithms developed by Fenestra Research Labs. All measurements were taken at baseline and again at each office visit. Parameters measured in both urine and saliva samples included: pH, $rH_2$ (a derived index of oxidative stress), ORP, r (resistivity), conductivity, surface tension, specific gravity, nitrates, nitrites, ammonias, and ureas. With regard to hydration, there are 39 measurements performed in conjunction with the Optimal Wellness Test. The parameters in Table 1 had relevant changes in their numbers among the subjects involved in the study. Generally speaking, these parameters were chosen because they relate to ionic content, Zeta potential, the cells, extracellular fluids, hydration indicators, the presence of reduced or oxidized bimolecular, and the first, in some cases even pre-symptomatic, stages of degeneration. Measuring parameters in saliva and urine can be indicative of the state of hydration in tissues and the body's ability to absorb nutrient and palliative chemicals and to dispose of toxins, metabolites, and tissue degradation residues, many of which stimulate further inflammation and pain. The results of the study showed that, on the one hand, there was no statistically significant change in any parameter relating to hydration measured for the placebo group. On the other hand, a very significant change in all parameters measured was seen in the water treating product group of approximately 32%.

With regard to oxygenation, oximetry is a noninvasive technique of measuring arterial blood oxygen saturation (Sao2). This measurement is the ratio of oxygenated hemoglobin in the total amount of hemoglobin in a blood sample. Oximetry is typically used to monitor a patient's oxygen saturation during surgery or in any clinical situations where there is a need to know how much oxygen is in circulation in the patient's blood stream. Each subject in the study had his or her oximetry values recorded at each office visit. The average number presented at baseline was 86% overall. The placebo group measured no significant changes from baseline to the last day of the study using oximetry measurements. The average on the last day of the study was 87% overall. In comparison, the water treating product group measured a significant improvement from baseline to week-1 in oximetry measurements. This significant change was approximately 13% overall. The average on the last day of the study for the water treating product group was 98% overall.

Regarding blood oxygen, subjects had arterial blood drawn at baseline, 1-week, 2-weeks, and 4-weeks intervals. Three 3.0 cc blood samples were collected and analyzed. The change in blood oxygen was measured using the average number between the three vials taken at each blood draw. On the one hand, statistical analysis of the study's data shows no significant improvement in the blood oxygen saturation as measured in arterial blood for the placebo group. On the other hand, statistical analysis of the study's data shows a significant improvement of approximately 12.8% overall in the blood oxygen saturation as measured in arterial blood samples in the water treating product group.

Additionally, nitrate numbers of the Optimal Wellness Test indicate a positive move in the wellness numbers of those in the water treating product study group of up to 18.8%. All subjects in the water treating product group showed an improvement in their nitrate numbers with the most significant improvements seen in subjects with their baseline first test numbers the farthest from the wellness range. This shows an improvement in the body's ability to remove urea stores before they can become nitrates and toxins. Extrapolation of data pertaining to nitrates indicates an increase in fluidity of substances in the cellular body resulting in decreased nitrate production and storage in subjects consuming water treated by the water treating product at about the second month of consumption. The reason for the length of time of consumption being necessary for nitrate production to decrease is believed to correspond to the increase of intracellular hydration numbers and the body's ability to create homeostasis. The study also indicates a change in the amount of toxins being stored in the intracellular body being decreased in all subjects using the water treating product. A scientific measurement of toxins in the body showed a significant improvement for these subjects. The mechanism for the removal of the toxins in the body is the movement of water as fluids throughout the body become more fluid and the body has a more anionic field. This anionic field allows for the cationic substances to be attracted and removed as waste products. No change was seen in the placebo group. In comparison, nitrate numbers of the Optimal Wellness Test indicated a positive move in the wellness numbers of those in the water treating product study group of up to 18.8%. All subjects in the water treating product group showed an improvement in their nitrate numbers with the most significant improvements seen in subjects with their baseline first test numbers the farthest from the wellness range. This shows an improvement in the body's ability to remove urea stores before they can become nitrates and toxins. The placebo group showed no significant changes in nitrate indicators for the duration of the study.

Also, the pH indicators provided within the Optimal Wellness Test indicated a positive move toward neutral pH in regards to the wellness parameter of those in the water treating product group of up to 27.2%. Many prior studies have shown the importance of maintaining neutral cellular chemistry for increasing one's ability to experience wellness. This shift in pH toward a more neutral cellular chemistry in the water treating product group may be due to the aforementioned chemical changes occurring in the reduction of nitrates and toxins.

During the study, the presence of heavy metals was tested using arterial blood drawn from each subject at baseline and on the last day of the study. The amount of these metals that should be present at the time of testing is 0.0 ppm. The placebo group measured no significant changes from baseline to the last day of the study overall. The average at baseline for the placebo group was:
- 29 ppm mercury
- 96 ppm lead
- 38 ppm cadmium
- 109 ppm aluminum
- 18 ppm nickel The average for the placebo group at the last day of the study was:
- 29 ppm mercury
- 95 ppm lead
- 38 ppm cadmium
- 110 ppm aluminum
- 20 ppm nickel In comparison, the water treating product group measured significant changes from baseline to the last day of the study overall. The average at baseline for the water treating product group was:
- 32 ppm mercury
- 89 ppm lead
- 35 ppm cadmium
- 105 ppm aluminum
- 14 ppm nickel The average at the last day of the study for the water treating product group was:
- 8 ppm mercury
- 52 ppm lead
- 11 ppm cadmium
- 56 ppm aluminum
- 6 ppm nickel As a result, the average removal of the following ppm of heavy metals in the water treating product group was:
- 24 ppm mercury
- 37 ppm lead
- 24 ppm cadmium
- 49 ppm aluminum
- 8 ppm nickel Also, statistical analysis of the study's data shows a significant improvement to the ATP, carbohydrate side of the energy cycle of an 11.1% improvement overall in the water treating product group. Statistical analysis of the study's data shows no significant change to the ATP, energy cycle in the placebo group.

Finally, clinical blood microscopy was performed on 25 subjects randomly chosen from the water treating product group who participated in the study. Arterial blood was drawn and placed between two glass slides and then analyzed and compared by a Certified Clinical Microscopy specialist. A significant improvement to the blood samples was seen in all 25 subjects tested.

In summary, the clinical human tests have demonstrated by statistical analysis that the treated water repeatably increased hydration by approximately 32% on average. The treated water also increased blood oxygenation by approximately 13.0% on average. The treated water also aided the elimination of toxins in the human body. The treated water cleansed cellular toxins such as nitrates and ureas from cells. Moreover, in the first such results obtained through human clinical studies, heavy metal toxins in humans drinking treated water were substantially reduced, for example, the presence of mercury was reduced by approximately 75%.

Considered in more detail, statistical analysis of the study's data shows a consistent result between the placebo and water treating product groups over time. Statistical analysis of the study's data showed a significant improvement in the cellular hydration of approximately 32% overall in the water treating product group. This number stayed consistently the same from the third week of the study through its last day. Statistical analysis of the study's data showed no significant changes in the cellular hydration of the placebo group. Furthermore, statistical analysis of the study's data showed a significant improvement of approximately 13.5% overall in the blood oxygen saturation as measured by oximetry in the water treating product group. Statistical analysis of the study's data showed no significant improvement in the blood oxygen saturation as measured by oximetry for the placebo group. Moreover, statistical analysis of the study's data showed a significant improvement of approximately 12.8% overall in the blood oxygen saturation as measured in arterial blood samples in the water treating product group. Statistical analysis of the study's data showed no significant improvement in the blood oxygen saturation as measured in arterial blood for the placebo group. Additionally, statistical analysis of the study's data showed a significant improvement in the removal of harmful nitrates, mercury, lead, cadmium, aluminum, and nickel in the water treating product group. Statistical analysis of the study's data showed no significant change in the removal of harmful nitrates, mercury, lead, cadmium, aluminum, or nickel in the placebo group. Based on these clinical comparisons and the complete lack of known adverse side effects, interactions, or contra-indications from the use of the water treating product, the product was shown to be a safe and highly effective means of treating water for increasing cellular hydration, oxygenation, and detoxification. Also, in a first ever human clinical study, the treated water also produced an approximately 11.1% increase in ATP which is produced when the cristae of the mitochondria combine food (sugar) with oxygen to provide the primary energy source for a cell.

While the foregoing description has been with reference to particular examples of the present invention, it will be appreciated by those skilled in the art that changes in these examples may be made without departing from the principles and spirit of the invention. For example, the initial 200× concentrate that is not used in processing can be substantially diluted to provide a dilute ionized liquid that can be added to treated water and consumed as a mineral supplement. Furthermore, treated water has also been demonstrated to increase hydration in other animals including mammals such as horses including thoroughbred race horses and other livestock such as cattle, which can be watered using untreated water flowed to watering troughs through the encapsulation device 70 and to which ionic minerals can be added. Additional applications are also contemplated. For example, the encapsulation device 40 can be modified to have neutral buoyancy or to eliminate the stem 44 such that a reusable capsule remains that may be placed in a bag containing water for transporting aquarium fish, for example. By way of a further example, a survival kit can incorporate an encapsulation device 40 and additional minerals to be added to untreated non-potable water to render the water potable, and the same principle can be expanded in scale to provide potable water during disaster relief if the normal supply of potable water is disrupted. Other examples are also contemplated such as formulating perishable products such as prepared foods, medicines, and cosmetics with treated water to increase shelf life. Accordingly, the scope of the present invention can only be ascertained with reference to the appended claims.

What is claimed is:

1. A product produced in accordance with a process comprising the steps of:
   a) adding mica to sulfuric acid in a ratio of approximately 1 gram of mica:approximately 5 ml of acid;
   b) boiling the mica and acid mixture for approximately 3.0 to 3.25 minutes;
   c) cooling, separating, and diluting the boiled liquid to obtain an approximately 5% concentration;

d) adding unprocessed approximately 99% by weight mica and approximately 1% by weight magnetite to the approximately 5% concentration liquid in a ratio of approximately 1 gram of mixture:approximately 5 ml of liquid;
e) heating the mica and magnetite and liquid mixture at approximately 150° F. for approximately 48 hours;
f) raising the temperature of the mica and magnetite and liquid mixture to approximately 420° F. for approximately 50 minutes;
g) ramping the temperature of the mica and magnetite and liquid mixture to approximately 860° F. for approximately 33 minutes;
h) reducing the temperature of the mica and magnetite and liquid mixture to approximately 640° F. for approximately 4 minutes;
i) decreasing the temperature of the mica and magnetite and liquid mixture to approximately 475° F. for approximately 2 minutes; and
j) cooling the mica and magnetite and liquid mixture to ambient temperature;
thereby producing an intermediate byproduct;
k) containing the intermediate byproduct in a stirring device; and
l) repeating steps d-k seventeen times using the intermediate byproduct produced at the conclusion of each repetition in the stirring device for the subsequent repetition.

2. The product according to claim 1, wherein the process further comprises the step of encapsulating the product for use in treating water.

3. The product according to claim 1, further comprising white Brazilian quartz crystal present in an approximate ratio of 1 gram of white Brazilian quartz:1-3 grams of product.

4. The product according to claim 1, further comprising rose quartz and white Brazilian quartz crystal present in an approximate ratio of 0.25 gram of rose quartz:0.25 gram of white Brazilian quartz:2.5 grams of product.

5. The product according to claim 1, further comprising amethyst and white Brazilian quartz crystal present in an approximate ratio of 0.25 gram of amethyst:0.25 gram of white Brazilian quartz:2.5 grams of product.

6. The product according to claim 1, further comprising reishi mushroom, amethyst, and white Brazilian quartz crystal present in an approximate ratio of 0.6 gram of reishi mushroom:0.25 gram of amethyst:0.25 gram of white Brazilian quartz:2.6 grams of product.

7. The product according to claim 1, further comprising lion's mane mushroom and white Brazilian quartz crystal present in an approximate ratio of 0.5 gram of lion's mane mushroom:0.25 gram of white Brazilian quartz:2.65 grams of product.

8. The product according to claim 1, further comprising Kunzite crystal and white Brazilian quartz crystal present in an approximate ratio of 0.5 gram of Kunzite crystal:0.25 gram of white Brazilian quartz:2.55 grams of product.

9. The product according to claim 1, further comprising obsidian and white Brazilian quartz crystal present in an approximate ratio of 0.25 gram of obsidian:0.25 gram of white Brazilian quartz:2.8 grams of product.

10. The product according to claim 1, further comprising tourmaline and white Brazilian quartz crystal present in an approximate ratio of 0.25 gram of tourmaline:0.5 gram of white Brazilian quartz:2.55 grams of product.

11. The product according to claim 1, further comprising ceramic powder in an approximate ratio of 0.1 to 0.3 grams of ceramic powder:3.0 grams of product.

12. The product according to claim 1 wherein the mica is black mica.

13. The product according to claim 1 wherein the process further comprises the step of exfoliating the mica prior to step a.

14. The product according to claim 1 wherein the liquid concentration is in the range of 6.5-7.0%.

15. The product according to claim 1 wherein a full spectrum heat lamp is used as a heat source for step e.

* * * * *